(12) United States Patent
Ukita et al.

(10) Patent No.: US 7,153,859 B2
(45) Date of Patent: Dec. 26, 2006

(54) CONDENSED POLYCYCLIC COMPOUNDS

(75) Inventors: Tatsuzo Ukita, Kobe (JP); Yoshihiro Terakawa, Osaka (JP); Kazuteru Wada, Amagasaki (JP); Aya Nakata, Kita-ku (JP); Atsuko Sakai, Wako (JP); Koji Ogawa, Kita-ku (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 232 days.

(21) Appl. No.: 10/486,088

(22) PCT Filed: Jul. 31, 2002

(86) PCT No.: PCT/JP02/07783

§ 371 (c)(1),
(2), (4) Date: Feb. 6, 2004

(87) PCT Pub. No.: WO03/016279

PCT Pub. Date: Feb. 27, 2003

(65) Prior Publication Data

US 2004/0204418 A1      Oct. 14, 2004

(30) Foreign Application Priority Data

Aug. 9, 2001  (JP) ............................. 2001-241502
Aug. 9, 2001  (JP) ............................. 2001-241517
Aug. 9, 2001  (JP) ............................. 2001/241521

(51) Int. Cl.
  *A61K 31/497*    (2006.01)
  *C07D 241/36*    (2006.01)
  *C07D 471/00*    (2006.01)
  *C07D 487/00*    (2006.01)

(52) U.S. Cl. ..................... 514/253.03; 544/344

(58) Field of Classification Search ..................... None
  See application file for complete search history.

(56) References Cited

U.S. PATENT DOCUMENTS 4,678,501 A   7/1987   Manning ....................... 71/92
6,005,106 A   12/1999  Ukita et al. ................. 544/237
6,011,060 A   1/2000   Laurent et al. ............. 514/473

FOREIGN PATENT DOCUMENTS

| EP | 0 557 016 A1 | 8/1993 |
|---|---|---|
| EP | 0 748 805 B1 | 12/1996 |
| JP | 2000-063275 | 2/2000 |
| WO | WO 97/22585 | 6/1997 |
| WO | WO 97/23457 | 7/1997 |
| WO | WO 98/02440 | 1/1998 |
| WO | WO 98/09961 | 3/1998 |
| WO | WO 98/14432 | 4/1998 |
| WO | WO 00/12503 | 3/2000 |
| WO | WO 02/00657 A2 | 1/2002 |
| WO | WO 02/38563 A2 | 5/2002 |
| WO | WO 02/094320 A1 | 11/2002 |
| WO | WO 02/094321 A1 | 11/2002 |

OTHER PUBLICATIONS

Anil K. Saxena et al., "Compounds Acting on the CNS: Part XXI—Synthesis of 2-Substituted 1,3,4,6,II,IIa-Hexahydro-2(H)pyrazino, etc.," Indian Journal of Chemistry, vol. 13, Mar. 1975, pp. 230-237.
J. Mol Cell Cardiol, vol. 21 (Supplement II) (1989), S.61.

*Primary Examiner*—Zachary C. Tucker
(74) *Attorney, Agent, or Firm*—Finnegan, Henderson, Farabow, Garrett & Dunner, L.L.P.

(57) ABSTRACT

The present invention provides a novel a condensed polycyclic compound useful as a phosphodiesterase 4 inhibitor, which is shown by the formula [I]:

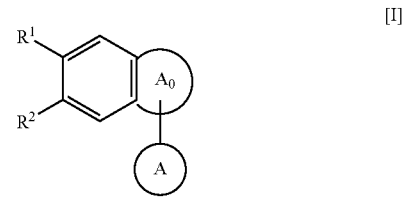

or a pharmaceutically acceptable salt thereof and a pharmaceutical composition containing the same.

9 Claims, No Drawings

CONDENSED POLYCYCLIC COMPOUNDS

This application was filed under 35 U.S.C. 371, and is the United States National Stage of PCT/JP02/07783, filed 31 Jul. 2002.

TECHNICAL FIELD

The present invention relates to a novel condensed polycyclic compounds (pyrazinoisoquinoline compounds or naphthalene compounds) having excellent inhibitory effects on phosphodiesterase 4 ("PDE4") and a pharmaceutical composition or a PDE4 inhibitor comprising the said compound as an active ingredient.

BACKGROUND ART

It is known that intracellular second messengers such as cAMP and cGMP are decomposed and inactivated by phosphodiesterase ("PDE"). Inhibition of PDE results in increase of intracellular cAMP and cGMP level. It is known that PDE can be classified into several isozymes each being different in terms of substrate (cAMP, cGMP) specificity, distribution in the body, and the like, and that, among isozymes, the type 4 PDE ("PDE4") decomposes cAMP specifically.

There also have been known that inhibition of PDE4 activity can block the release of inflammatory mediator (J. Med. Cell. Cardiol. 21 (Suppl. II), S61 (1989), PDE4 inhibitor restrains the production of TNFα that is a cytokine released from mononuclear phagocytes in response to immunostimulation, and is useful in treatment of various inflammatory diseases and the like (WO98/14432, WO98/09961, U.S. Pat. No. 6,011,060, WO98/02440, WO97/23457 and WO97/22585).

Theophylline, a representative PDE inhibitor, has hitherto been used in treatment of asthma. However, the PDE inhibitory activity of theophylline is non-specific, and it shows cardiotonic and central activity in addition to the bronchial smooth muscle relaxation activity. Thus, one must pay careful attention to this drug in view of such side effects. Accordingly, it has been desired to develop a new medical agent which can selectively inhibit PDE4 among PDE isozymes, which largely exists especially in bronchial smooth muscle and inflammatory cells. Such an agent is expected to be a promising medicine for prophylaxis and treatment of asthma or inflammatory diseases.

On the other hand, a certain compounds of pyrazinoisoquinoline type, specifically 8,9-dimethoxy-6-phenyl-1,3,4,6,11,11a-hexahydro-2H-pyrazino[1,2-b]isoquinoline shows central nervous system depresssant and hypotensive effects. Indian J. Chem., vol. 13, 230–237 (1975)

As a naphthalene-type compound having PDE4 inhibitory activity, U.S. Pat. No. 6,005,106 discloses a compound wherein a nitrogen atom is directly attached to the pyridine ring at position 1 on the naphthalene moiety, but never discloses a compound wherein a carbon atom is directly attached to the pyridine ring at position 1 on the naphthalene moiety.

DISCLOSURE OF INVENTION

The present inventors have intensively studied and found that a condensed polycyclic compound having a pyrazinoisoquinoline or naphthalene moiety has excellent anti-PDE4 activity and established the present invention, as hereinafter described.

The present invention provides a novel condensed polycyclic compound (a pyrazinoisoquinoline compound or a naphthalene compound) useful as a PDE4 inhibitor. The present invention also provides a pharmaceutical composition comprising said compound as an active ingredient.

Thus, the present invention is related to a condensed polycyclic compound of the formula [I]:

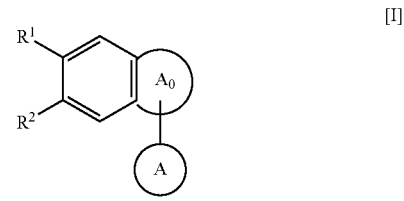

wherein,
$R^1$ and $R^2$ are the same or different and each a group selected from a hydroxy group and a lower alkoxy group;
ring $A_0$ is a group of the formula:

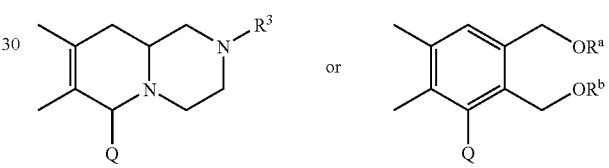

ring A is:
(1) a substituted or unsubstituted benzene ring or a substituted or unsubstituted aromatic heterocyclic ring, when ring $A_0$ is a group of the formula:

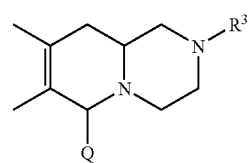

or
(2) a group of the formula:

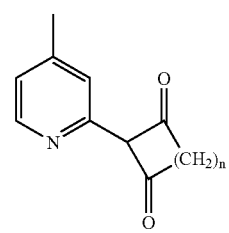

wherein n is an integer of 1 to 6, when ring $A_0$ is a group of the formula:

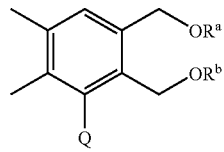

$R^3$ is:
(1) a hydrogen atom, a group of the formula: —(CH²)$_m$—$R^{31}$ or a group of the formula: —CO—$R^{32}$, when ring A is a substituted benzene ring or a substituted or unsubstituted aromatic heterocyclic group; or
   (2) a group of the formula: —(CH$_2$)$_m$—$R^{31}$ or a group of the formula: —CO—$R^{32}$, when ring A is an unsubstituted benzene ring;
$R^{31}$ is a hydrogen atom, an aryl group, a hydroxy group, an amino group, a carboxyl group, a lower alkoxycarbonyl group or a lower alkylthio group;
$R^{32}$ is an aryl group, a lower alkyl group, a hydroxy-lower alkyl group or an amino-lower alkyl group;
m is an integer of 1 to 6;
Q is a single bond linked to ring A; and
$R^a$ and $R^b$ are the same or different and each a group selected from a hydrogen atom and an acyl group,
or a pharmaceutically acceptable salt thereof.

The present invention also relates to a pharmaceutical composition or a PDE4 inhibitor comprising a compound of the present invention as an active ingredient.

BEST MODE FOR CARRYING OUT THE INVENTION

When the compound [I] of the present invention has an aryl group, examples of the aryl group include a mono-, bi- or tri-cyclic aryl group of 6 to 14 carbon atoms such as a phenyl group, a naphthyl group, an anthryl group and a phenanthryl group. A phenyl group is preferred above all. Examples of the acyl group for $R^a$ and $R^b$ of compound [I] include a lower alkanoyl group and an acetyl group is preferred. The symbol "an" refers to an integer of 1 to 6, preferably 2 to 4, and more preferably 3.

When ring A is a substituted or unsubstituted aromatic heterocyclic group, examples of said aromatic heterocyclic group include a 5- to 6-membered monocyclic aromatic heterocyclic group containing 1 to 3 nitrogen atoms, and specifically, pyridine ring, pyrimidine ring, pyrazine ring, pyridazine ring and the like.

When ring A is a substituted benzene ring or a substituted aromatic heterocyclic ring, the benzene or aromatic heterocyclic ring may have 1 to 3 substituents selected from, for example, a lower alkoxy group (methoxy, ethoxy, isopropyloxy group, etc.), a hydroxy group and a halogen atom (chlorine, fluorine, bromine, etc.).

Among the objective compounds (I) of the present invention, preferred compounds are condensed polycyclic compounds wherein ring $A_0$ is a group of the formula:

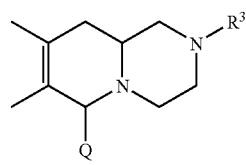

and examples thereof include pyrazinoisoquinoline compounds shown by the formula [I-A]:

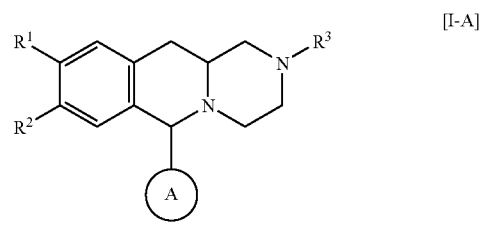

wherein each symbol has the same meaning as defined above. More preferred compounds of the formula [1-A] are those wherein $R^1$ and $R^2$ are the same or different and each an alkoxy group; ring A is a benzene ring substituted by 1 to 3 groups selected from a lower alkoxy group, a hydroxy group and a halogen atom; and $R^3$ is a hydrogen atom. Among the compounds of the formula [1-A] above, those wherein $R^1$ and $R^2$ are the same or different and each a group selected from a methoxy group and an ethoxy group; ring A is a benzene ring substituted by 1 to 3 groups selected from an isopropyloxy group, a hydroxy group and a halogen atom; and $R^3$ is a hydrogen atom are still more preferred. Especially preferred compound above all is 6-[4-(isopropyloxy)phenyl]-8,9-dimethoxy-1,3,4,6,11,11a-hexahydro-2H-pyrazino[1,2-b]isoquinoline or 6-(4-fluorophenyl)-8,9-dimethoxy-1,3,4,6,11,11a-hexahydro-2H-pyrazino[1,2-b]isoquinoline.

Another preferred compounds of the formula [I] of the present invention are condensed polycyclic compounds wherein ring $A_0$ is a group of the formula:

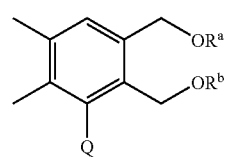

and examples thereof include naphthalene compounds shown by the formula [1-B]

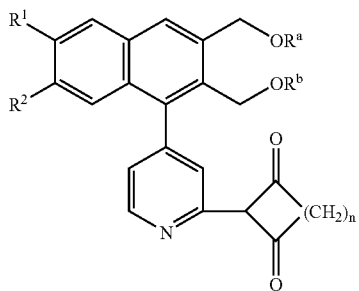

[I-B]

wherein each symbol has the same meaning as defined above. Among the compounds above, those of the formula [1-B], wherein $R^1$ and $R^2$ are the same or different and each a lower alkoxy group; $R^a$ and $R^b$ are the same or different and each a group selected from an acetyl group and a hydrogen atom; and n is an integer of 3 are more preferred. Even more preferred compounds of the formula [I-B] are those wherein $R^1$ and $R^2$ are the same or different and each a lower alkoxy group; $R^a$ and $R^b$ are each a hydrogen atom, and n is 3. Among them, especially preferred compound is 6,7-dimethoxy-1-[2-(1,3-dioxocyclohexan-2-yl)pyridin-4-yl]-2,3-bis(hydroxymethyl)naphthalene.

Further, the present invention encompasses within its scope a PDE4 inhibitory agent (PDE4 inhibitor) comprising a pyrazinoisoquinoline compound (derivative) of the formula [I-C]:

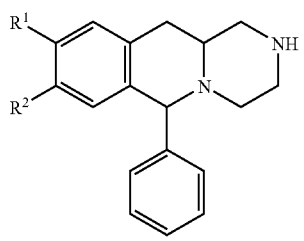

[I-C]

wherein $R^1$ and $R^2$ are the same or different and each a hydroxy group or a lower alkoxy group, or a pharmaceutically acceptable salt thereof as an active ingredient.

As the compounds [I-C] above, those wherein $R^1$ and $R^2$ are the same or different and each a lower alkoxy group are preferred and those wherein $R^1$ and $R^2$ are the same or different and each a group selected from a methoxy group and an ethoxy group are more preferred. Especially preferred compound is 8,9-dimethoxy-6-phenyl-1,3,4,6,11,11a-hexahydro-2H-pyrazino[1,2-b]isoquinoline.

When a compound [I] of the present invention has an asymmetric carbon atom(s) at the substituent(s) in groups $R^1$, $R^2$ and $R^3$ and/or in ring A and/or at the 1,3,4,6,11,11a-hexahydro-2H-pyrazino[1,2-b]isoquinoline moiety, it may exist in any forms of plural stereoisomers (diastereoisomers, enantiomers) owing to said asymmetric carbon atom(s), and the present invention also includes any one of these stereoisomers or a mixture thereof.

The present compound of the formula [I] or [I-C], or a pharmaceutically acceptable salt thereof has an excellent PDE4 inhibitory activity and is useful in prophylaxis or treatment of various PDE4-associated diseases. Examples of such diseases include inflammatory disease and allergic disease of various types, specifically, asthma, chronic obstructive pulmonary disease (COPD), chronic bronchitis, atopic dermatitis, urticaria, allergic rhinitis, allergic conjunctivitis, vernal conjunctivitis, eosinophilia, psoriasis, rheumatoid arthritis, septic shock, ulcerative colitis, Crohn's disease, reperfusion injury, chronic glomerulonephritis, endotoxic shock, adult respiratory distress syndrome, osteoarthropathy, and the like. The compounds [I], [I-C] or pharmaceutically acceptable salts thereof of the present invention have potent bronchoconstriction inhibitory activity and are useful as a bronchoconstriction inhibitory agent.

In addition, the present inventors have found that compounds having PDE4 inhibitory activity are useful for accelerating bone fracture healing or in regenerative treatment of chondropathia (e.g. osteoarthritis) (Japanese Patent Appln. Nos. 2001-154064, 2001-154048, corresponding to PCT/JP02/094321 and PCT/JP02/094320, respectively). Accordingly, the compounds of the formula [I] or [I-C] or a pharmaceutically acceptable salt thereof of the present invention are useful as an active ingredient of a composition for accelerating bone fracture healing and treating chondropathia cartilage diseases (e.g., osteoarthritis).

The present compounds [I] and compounds [I-C] inhibit PDE4 selectively and hence would have few side effects. Further, the compounds [I] and compounds [I-C) of the present invention have the merit of being less toxic, and highly safe as a medicine. For example, 8,9-dimethoxy-6-phenyl-1,3,4,6,11,11a-hexahydro-2H-pyrazino[1,2-b]-isoquinoline was subcutaneously administered to a mouse (BDF1 strain, male, n=3) in a single dose (100 mg/kg) and the progress was checked for 1 day. As a result, no death was observed.

The present compounds [I] and compounds [I-C] of the present invention can be clinically used either in the free form or in the form of a pharmaceutically acceptable salt thereof. The pharmaceutically acceptable salt of the compound [I] includes a salt with an inorganic acid such as hydrochloride, sulfate, phosphate or hydrobromide, or a salt with an organic acid such as acetate, fumarate, oxalate, citrate, methanesulfonate, benzenesulfonate, tosylate or maleate. Besides, when the above-mentioned compound has a carboxyl group(s) in its molecule, examples of the pharmaceutically acceptable salt include salts with a base such as alkaline metal (e.g., sodium salt, potassium salt) or alkaline earth metal (e.g., calcium salt).

The compound [I], compound [I-C] or a salt thereof of the present invention includes either intramolecular salt or an additive thereof, and solvates or hydrates thereof.

The present compound [I], compound [I-C], or a pharmaceutically acceptable salt thereof can be administered either orally or parenterally, and can be formulated into a conventional pharmaceutical preparation such as tablets, granules, capsules, powders, injections or inhalants.

The dose of the compound [I], compound [I-C], or a pharmaceutically acceptable salt thereof of the present invention may vary in accordance with the administration routs, and the ages, weights and conditions of the patients. For example, when administered in an injection preparation, it is usually in the range of about 0.01 to 10 mg/kg/day, preferably in the range of about 0.03 to 3 mg/kg/day. When administered in an oral preparation, it is usually in the range of about 0.1 to 30 mg/kg/day, preferably in the range of 0.3 to 10 mg/kg/day.

The compound [I] or [I-C] of the present invention can be prepared in the following manner.

Preparation of Pyrazinoisoquinoline Compounds [I-A]

Among the present condensed polycyclic compounds of the formula [I], pyrazinoisoquinoline compounds [I-A] wherein $R^3$ is a group of the formula: —$(CH_2)_m$—$R^{31}$ (compound [I-$A_1$]) or $R^3$ is a group of the formula: —CO—$R^{32}$ (compound [I-$A_2$]) can be prepared, for example, in accordance with the reaction scheme below.

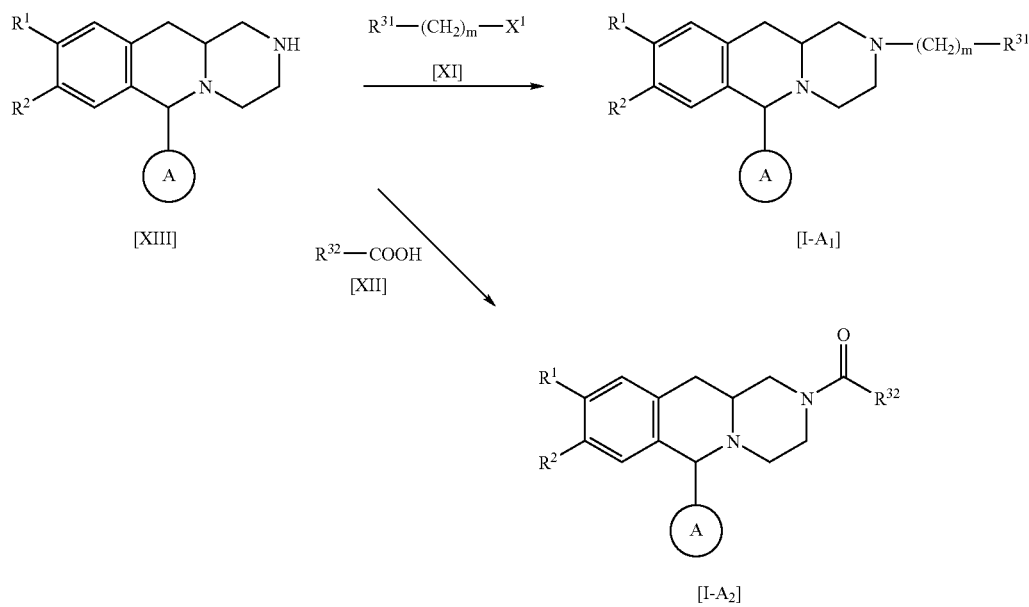

wherein $X^1$ is a leaving group such as a halogen atom and the rest of the symbols have the same meaning as defined above.

Among the present compounds [I-A] above, the compounds [I-$A_1$] wherein $R^3$ of the formula [I-A] is a group of the formula: —$(CH_2)_m$—$R^{31}$ can be prepared by reacting a compound [XIII] and a compound [XI]. This reaction can be carried out in the presence of an appropriate base (e.g., triethylamine, potassium carbonate, etc.). The base can be used in an amount of 1 to 3 moles, preferably, 1.2 to 1.5 moles to one mole of the compound [XIII] or the compound [XI]. The reaction can be conducted at −10 to 100° C., preferably, 0 to 30° C.

Among the present compounds [I-A] above, compounds [I-$A_2$] wherein $R^3$ of the formula [I-A] is a group of the formula: —CO—$R^{32}$ can be prepared by reacting a compound [XIII] and a compound [XII]. The reaction between the compound [XIII] and the compound [XII] to yield the compound [I-$A_2$] can be carried out in the presence of a conventional condensing agent (e.g., dicyclohexylcarbodiimide, 1-ethyl-3-(3-dimethylaminopropyl)carbodiimide hydrochloride/1-hydroxybenzotriazole monohydrate, etc.).

The condensing agent can be used in an amount of 1 to 5 moles, preferably, 1.1 to 1.5 moles to one mole of the compound [XIII] or the compound [XII]. The reaction can be conducted at −10 to 100° C., preferably, 0 to 30° C.

The compounds [I-$A_2$] can also be prepared by treating a compound [XII] with a halogenating agent (e.g., thionyl chloride, oxalyl chloride) to convert the same into corresponding acid halide, and reacting the resultant acid halide with a compound [XIII] in the presence of a base (e.g., triethylamine).

The halogenating agent can be used in an amount of 1 to 3 moles, preferably, 1.1 to 1.5 moles to one mole of the compound [XII]. The base can be used in an amount of 1 to 4 moles, preferably, 1.1 to 1.5 moles to one mole of the acid halide or the compound [XIII] above. The reaction can proceed at −20 to 40° C., preferably, 0 to 30° C.

Furthermore, the compounds [I-$A_2$] can also be prepared by treating a compound [XII] with an activating agent (e.g., isobutyl chlorocarbonate, ethyl chlorocarbonate, etc.) and a base (e.g., triethylamine, N-methylmorpholine, diisopropylethylamine, etc.) to convert the same into corresponding mixed acid anhydride, and reacting the resultant mixed acid anhydride with a compound [XIII].

The activating agent can be used in an amount of 1 to 4 moles, preferably, 1.1 to 1.5 moles to one mole of the compound [XII]. The base can be used in an amount of 1 to 4 moles, preferably, 1.1 to 1.5 moles to one mole of compound [XII]. The reaction can proceed at −50 to 50° C., preferably, −20 to 30° C.

The intermediates of the formula [XIII] for preparing the present compound [I-A] can be prepared in accordance with, for example, the reaction scheme below.

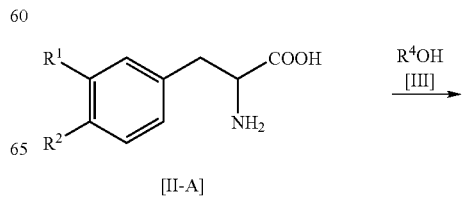

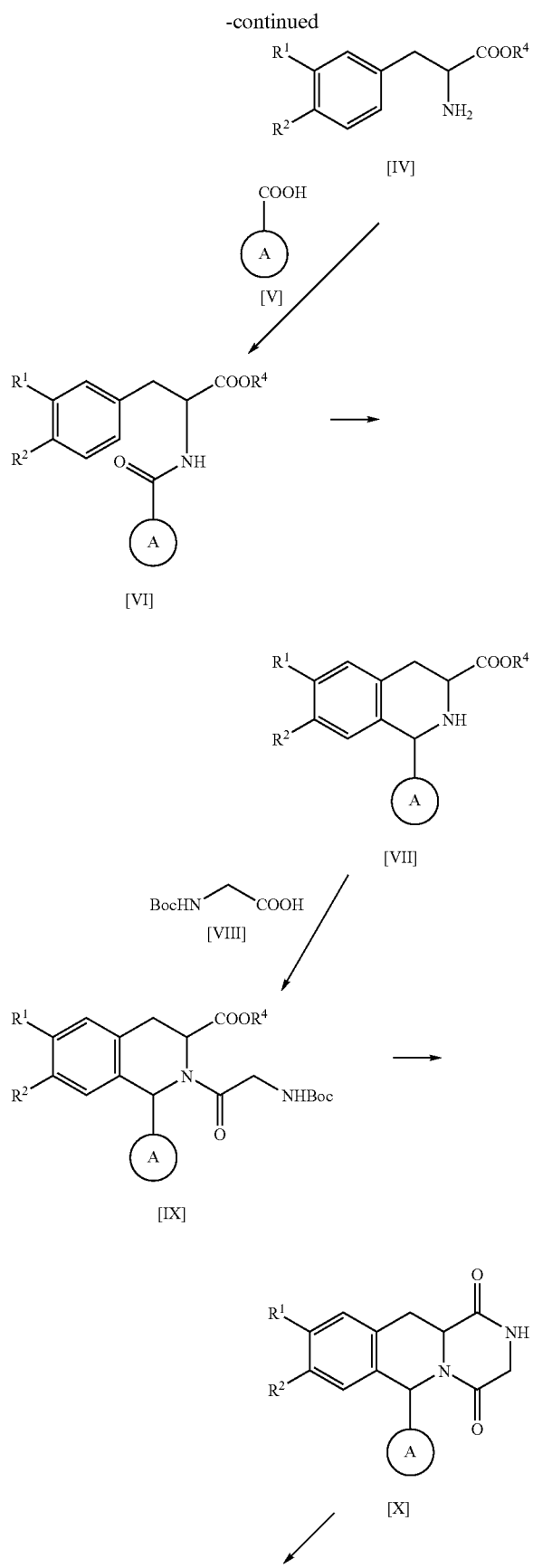

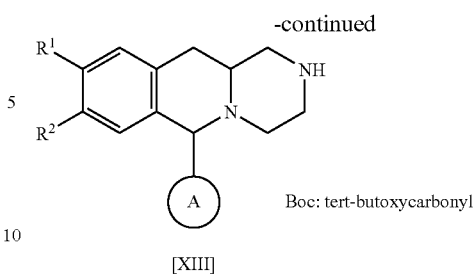

wherein $R^4$ is a lower alkyl, and the rest of the symbols have the same meanings as defined above.

The reaction wherein a compound [IV] is prepared from a compound [II-A] can be carried out by a conventional esterification reaction, for example, in the presence of ethanol/acetyl chloride, ethanol/thionyl chloride, ethanol/hydrogen chloride, etc.

The reaction wherein a compound [VI] is prepared from a compound [IV] and a compound [V] can be carried out by using a conventional condensing agent (e.g., dicyclohexylcarbodiimide, 1-ethyl-3-(3-dimethylaminopropyl)carbodiimide hydrochloride/1-hydroxybenzotriazole monohydrate, etc.).

The reaction wherein a compound [VII] is prepared from a compound [VI] can be carried out in the presence of a conventional reducing agent (e.g., platinum oxide/hydrogen, palladium-carbon/hydrogen, etc.) after condensation of these compounds using phosphorus oxychloride or phosphorus pentachloride.

The reaction wherein a compound [IX] is prepared from a compound [VII] and a compound [VIII] can be carried out by using a conventional condensing agent (e.g., carbonyldiimidazole, etc.). Alternatively, a compound [IX] can be prepared by treating a compound [VIII] with an activating agent (e.g., isobutyl chlorocarbonate, ethyl chlorocarbonate, etc.) and a base (e.g., triethylamine, N-methylmorpholine, etc.) to convert the same into a mixed acid anhydride, and reacting the resultant mixed acid anhydride with a compound [VII].

The intramolecular cyclization of a compound [IX] to give a compound [X] can be conducted by treating the compound [IX] with an acid (e.g., trifluoroacetic acid, hydrochloric acid, etc.) followed by heating.

The reaction wherein a compound [X] is reduced to give the compound [XIII] can be carried out in the presence of an appropriate reducing agent (e.g., borane-dimethylsulfide complex, lithium aluminum hydride, and bis(2-methoxyethoxy)aluminum hydride, etc.

Among compounds of the formula [XIII], those wherein ring A is a substituted benzene ring or a substituted- or unsubstituted-aromatic heterocyclic group (compounds [1-$A_3$]) fall within the scope of the objective compounds of the present invention.

Preparation of Naphthalene Compounds [I-B]

Among the present compounds of the formula [I], naphthalene compounds [I-B] can be prepared, for example, in accordance with the reaction scheme below.

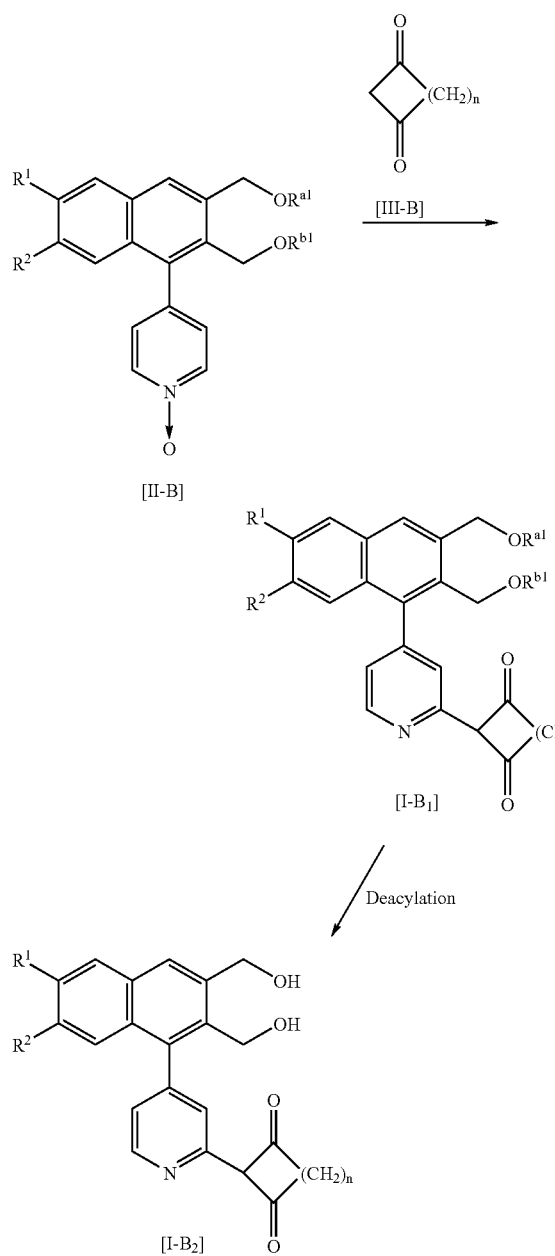

wherein $R^{a1}$ and $R^{b1}$ are the same or different and each an acyl group, and the rest of the symbols have the same meaning as defined above.

Among the present compounds of the formula [I-B] above, compounds [I-B$_1$] wherein $R^a$ and $R^b$ of the formula [I-B] are each an acyl group can be prepared by reacting a compound [II-B] with a compound [III-B]. This reaction can be carried out in the presence of a dehydrating agent (e.g., acetic anhydride, trifluoroacetic anhydride, etc.) at temperature attainable by warming/heating.

Among the present compounds of the formula [I-B] above, compounds [I-B$_2$] wherein $R^a$ and $R^b$ of the formula [I-B] are each a hydrogen atom can be prepared by subjecting a compound [I-B$_1$] to a conventional deacylation reaction. For example, the deacylation reaction can be carried out in the presence of an appropriate nucleophilic reagent (e.g., sodium methoxide, sodium ethoxide, sodium hydroxide, lithium hydroxide, etc.). The nucleophilic reagent can be used in an amount of 1 to 4 moles, preferably, 1.2 to 2 moles to one mole of the compound [I-B$_1$]. The reaction can be conducted with ice-cooling or at room temperature, and proceeds preferably at 5 to 20° C.

The compound [II-B] that is an intermediate for preparing compound [I-B] can be prepared in accordance with the method taught in JP-5-229987, A.

Preparation of Pyrazinoisoquinoline Compounds
[I-C]

The pyrazinoisoquinoline compounds [I-C] of the present invention can be prepared in a manner similar to that described in the case of compounds [I-A] above, for example, using a compound [IV] and a corresponding starting compound of the formula [V] wherein ring A is an unsubstituted benzene ring.

The aforementioned compounds [I] and compounds [I-C] of the present invention can also be prepared by further converting a substituent(s) in $R^1$, $R^2$ and $R^3$ and/or in ring A of the compounds obtained as heretofore described into another intended substituents. The method for converting substituents can be selected appropriately depending on the kinds of the intended substituent(s). For example, an objective compound of the formula [I] (or [I-C]) wherein $R^1$ and/or $R^2$ is a lower alkoxy group can be prepared by reacting a corresponding compound of the formula [I] wherein $R^1$ and/or $R^2$ is a hydroxy group with an alkylating agent (e.g., dimethyl sulfate, methyl halide, etc.) in the presence of a base (e.g., sodium hydroxide, sodium hydride, potassium carbonate, sodium methoxide, etc.).

The alkylating agent can be used in an amount of 1 to 8 moles, preferably, 1.2 to 2.2 moles to one mole of the compound [I] (or compound [I-C]). The reaction can proceed at 0 to 50° C., preferably at 10 to 40° C.

The compounds [I] or compounds [I-C] thus obtained can optionally be converted into pharmaceutically acceptable salts in a conventional manner in the art.

In the above-mentioned processes for preparing objective compounds [I] or compounds [I-C], not only the starting and intermediate compounds illustrated in the description and reaction schemes above but also salts or reactive derivatives thereof are also available, which do not adversely affect the reaction. Examples of such salts include salts with a metal such as sodium, potassium, lithium, calcium, magnesium, and the like; an organic base such as pyridine, triethylamine or diisopropylethylamine; an inorganic acid such as hydrochloric acid, sulfuric acid, nitric acid, hydrobromic acid or phosphoric acid; and an organic acid such as acetic acid, oxalic acid, citric acid, benzenesulfonic acid, benzoic acid, malonic acid, citric acid, formic acid, fumaric acid, maleic acid, methanesulfonic acid, p-toluenesulfonic acid or trifluoroacetic acid.

Furthermore, when a compound [I] or a compound [I-C] of the present invention, or a starting compound contains a functional group(s), the respective functional groups can be used either in the form as illustrated above or in the protected from by introducing an appropriate protecting group, which may be removed when it become unnecessary.

Respective reactions above can be carried out without or with an appropriate solvent. Any solvents can be used without limitation as far as it does not adversely affect the reaction, and can be selected from, for example, dioxane, ethylene glycol dimethyl ether, dimethylacetamide, dimethylformamide, hexamethylphosphoric triamide (HMPA), hexamethylphosphorous triamide (HMPT), benzene, tetrahydrofuran, toluene, xylene, ethyl acetate, lower alcohol (methanol, ethanol, isopropanol, etc.), dimethyl chloride, chloroform, carbon tetrachloride, 1,3-dimethyl-2-imidazolidinone, acetic acid, diethyl ether, diisopropyl ether, dimethoxyethane, dimethyl sulfoxide, acetone, methylethyl ketone, acetonitrile, water, and a mixture thereof.

When herein used with regard to the present invention, the term "lower alkyl group" means a straight- or branched-chain alkyl group having 1 to 6 carbon atoms, preferably 1 to 4 carbon atoms. The term "lower alkoxy group" means a straight- or branched-chain alkoxy group having 1 to 6 carbon atoms, preferably 1 to 4 carbon atoms. The term "halogen atom" means fluorine, chlorine, bromine or iodine atom. The term "acyl group" means a lower alkanoyl group and examples thereof include a straight- or branched-chain acyl group having 1 to 6 carbon atoms, preferably 2 to 4 carbon atoms. The term "lower alcohol" means alcohols of 1 to 6 carbon atoms (e.g., methanol, ethanol, isopropanol, etc.

EXAMPLES

Specific examples of the present compounds (I) prepared by the respective methods illustrated above are shown below for purposes of illustration and not limitation.

Example 1

(1) 2-Amino-3-(3,4-dihydroxyphenyl)propanoic acid (98.6 g) is dissolved in formic acid (900 ml), and thereto is added acetic anhydride (300 ml). The mixture is stirred at room temperature for 3 hours. The reaction solution is concentrated under reduced pressure, and to the resulting residue is added distilled water, and the mixture is further concentrated under reduced pressure. The residue is dissolved in distilled water (150 ml), and thereto are added a 10M aqueous sodium hydroxide solution (150 ml) and dimethyl sulfate (95 ml) under ice-cooling. To the mixture are further added three portions of dimethyl sulfate (totally 285 ml) every 30 minutes, during which a 10M aqueous sodium hydroxide solution (290 ml) is added dropwise, and the reaction temperature is kept at below 40° C., and the pH value is kept at pH 5 to 9. The mixture is stirred at room temperature overnight, and then 10M aqueous sodium hydroxide solution (50 ml) is added thereto. The mixture is further stirred at room temperature for 30 minutes. The pH value of the mixture is adjusted to pH 2 with sulfuric acid, and to the mixture is added ethyl acetate. The organic layer is dried over magnesium sulfate, and concentrated under reduced pressure. The residue is suspended in ethanol (1300 ml), and thereto is added dropwise acetyl chloride (280 ml) under ice-cooling. The mixture is stirred at room temperature for 3 days. The solvent is evaporated under reduced pressure, and methylene chloride is added to the residue. The organic layer is washed with an aqueous potassium carbonate solution, dried over magnesium sulfate, and concentrated under reduced pressure to give ethyl 2-amino-3-(3,4-dimethoxyphenyl)propionate (111 g) as oil.

MS (m/z): 253 (M$^+$)

(2) The compound obtained in the above (1) (111 g) and triethylamine (73.6 ml) are dissolved in methylene chloride (300 ml), and thereto is added dropwise benzoyl chloride (51.1 ml) under ice-cooling. Saturated aqueous sodium hydrogen carbonate solution is added, and the organic layer is washed with saturated brine, dried over magnesium sulfate, and concentrated under reduced pressure. The precipitated crystals are collected by filtration with diethyl ether to give ethyl 3-(3,4-dimethoxyphenyl)-2-(phenylcarbonylamino)propionate (144 g).

M.p.: 82–83° C.

MS (m/z): 357 (M$^+$)

(3) The compound obtained in the above (2) (71.5 g) is dissolved in phosphorus oxychloride (200 ml), and the mixture is heated under reflux overnight. The phosphorus oxychloride is removed by evaporation, and the residue is diluted with methylene chloride. The mixture is washed with aqueous potassium carbonate solution, dried over magnesium sulfate, and concentrated under reduced pressure. The residue is dissolved in ethanol, and thereto is added conc. hydrochloric acid (20 ml), and further concentrated under reduced pressure. The residue is dissolved in methanol (200 ml), and thereto is added platinum dioxide (1 g). The mixture is stirred under pressure of hydrogen gas (3 atoms) at room temperature for 4 hours. The insoluble materials are removed by filtration, and the filtrate is concentrated under reduced pressure. The residue is dissolved in chloroform, washed with a saturated aqueous sodium hydrogen carbonate solution and a saturated brine, dried over magnesium sulfate, and concentrated under reduced pressure. The precipitated crystals are collected by filtration to give 6,7-dimethoxy-1-phenyl-3-ethoxycarbonyl-1,2,3,4-tetrahydroisoquinoline (54.4 g).

M.p.: 215–217° C. (decomp.)

MS (m/z): 341 (M$^+$)

(4) 2-[(tert-Butoxy)carbonylamino]acetic acid (21.6 g) is dissolved in tetrahydrofuran (75 ml), and thereto are added dropwise triethylamine (18.7 ml) and isobutyl chloroformate (17.4 ml) at −20° C., and the mixture is stirred at −10° C. for 5 minutes. To the mixture is added dropwise a suspension of the compound obtained in the above (3) (38.2 g) in tetrahydrofuran (110 ml), and the mixture is stirred at room temperature overnight. The reaction solution is concentrated under reduced pressure, and extracted with chloroform. The extract is washed with a saturated aqueous sodium hydrogen carbonate solution and a saturated brine, dried over magnesium sulfate, and concentrated under reduced pressure. The resultant was crystallized from diethyl ether, and the resulting crystals are collected by filtration to give 2-{2-[(tert-butoxy)carbonylamino]acetyl}-6,7-dimethoxy-1-phenyl-3-ethoxycarbonyl-1,2,3,4-tetrahydroisoquinoline (31.7 g).

M.p.: 166–167° C.

MS (m/z): 498 (M$^+$)

(5) To the compound obtained in the above (4) (31.7 g) is added trifluoroacetic acid (60 ml) under ice-cooling, and the mixture is stirred for one hour. The reaction solution is concentrated under reduced pressure, and the resultant is dissolved in chloroform, and neutralized with triethylamine. The mixture is washed with a saturated aqueous sodium hydrogen carbonate solution and a saturated brine, dried over magnesium sulfate, and concentrated under reduced pressure. The residue is dissolved in toluene (350 ml), and the mixture is heated under reflux for 3 hours. The solvent is removed by evaporation, and the precipitates are collected by filtration with diethyl ether to give 8,9-dimethoxy-6-phenyl-2,3,11,11a-tetrahydro-6H-pyrazino[1,2-b]isoquinoline-1,4-dione (20.6 g).

M.p.: 265–267° C.

MS (m/z): 352 (M$^+$)

(6) Under nitrogen atmosphere, borane-dimethylsulfide complex (22.7 ml) is cooled with ice, and thereto is added dropwise a suspension of the compound obtained in the above (5) (20 g) in tetrahydrofuran (500 ml). The mixture is heated under reflux overnight, and thereto is added a 6M hydrochloric acid (50 ml), and the solvent is removed by evaporation under reduced pressure. The residue is diluted with chloroform, washed with aqueous sodium hydroxide solution, dried over magnesium sulfate, and concentrated under reduced pressure. The resulting residue is purified by column chromatography on silica gel (eluent; chloroform:methanol=9:1). The resulting crystals are dissolved in a mixture of chloroform and methanol, and thereto is added a 4M hydrochloric acid in ethyl acetate, and the solvent is removed by evaporation under reduced pressure. The precipitates are collected by filtration with ethanol to give 8,9-dimethoxy-6-phenyl-1,3,4,6,11,11a-hexahydro-2H-pyrazino[1,2-b]isoquinoline dihydrochloride (7.6 g).

M.p.: 220–224° C. (decomp.)

MS (m/z): 324 (M+)

(7) 8,9-Dimethoxy-6-phenyl-1,3,4,6,11,11a-hexahydro-2H-pyrazino[1,2-b]isoquinoline dihydrochloride (the compound obtained in Example 1-(6)) (2 g) is dissolved in N,N-dimethylformamide (10 ml), and thereto are added potassium carbonate (2.8 g) and benzyl bromide (0.7 ml), and the mixture is stirred at room temperature for 3 hours. The reaction solution is diluted with chloroform, washed with a saturated aqueous sodium hydrogen carbonate solution, dried over magnesium sulfate, and concentrated under reduced pressure. The precipitates (1.2 g) are dissolved in chloroform, and thereto is added a 4M hydrochloric acid in ethyl acetate, and the solvent is removed by evaporation under reduced pressure. The resultant is recrystallized from ethanol to give 8,9-dimethoxy-2-benzyl-6-phenyl-1,3,4,6,11,11a-hexahydro-2H-pyrazino[1,2-b]isoquinoline dihydrochloride (1.2 g).

M.p.: 198–203° C. (decomp.)

MS (m/z): 414 (M+)

Example 2

(1) Ethyl 2-amino-3-(3,4-dimethoxyphenyl)propionate (the compound obtained in Example 1-(1)) (15.2 g), 4-isopropyloxybenzoic acid (10.8 g), and 1-hydroxybenzotriazole monohydrate (9.2 g) are dissolved in methylene chloride (120 ml), and thereto is added 1,3-dicyclohexylcarbodiimide (12.4 g) under ice-cooling, and the mixture is stirred at room temperature overnight. The insoluble materials are removed by filtration, and the filtrate is washed with a saturated aqueous sodium hydrogen carbonate solution and a saturated brine, dried over magnesium sulfate, and concentrated under reduced pressure. The precipitated crystals are collected by filtration with diethyl ether to give ethyl 3-(3,4-dimethoxyphenyl)-2-{[4-(isopropyloxy)phenyl]carbonylamino}propionate (24.2 g).

M.p.: 126–128° C.

MS (m/z): 415 (M+)

(2) The compound obtained in the above (1) is treated in a similar manner as in Example 1-(3) to —(6) to give 6-[4-(isopropyloxy)phenyl]-8,9-dimethoxy-1,3,4,6,11,11a-hexahydro-2H-pyrazino[1,2-b]-isoquinoline dihydrochloride (1 g).

M.p.: 180–185° C. (decomp.)

MS (m/z): 382 (M+)

Examples 3–8

The corresponding starting compounds are treated in a similar manner as in Example 1-(1) to -(6) or in Example 2 to give the compounds as listed in Table 1.

TABLE 1

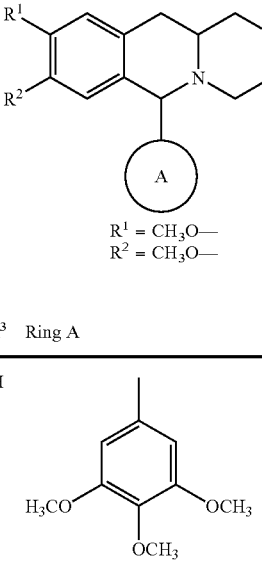

$R^1 = CH_3O—$
$R^2 = CH_3O—$

| Ex. No. | $R^3$ | Ring A | Physiochemical properties |
|---|---|---|---|
| 3** | H | 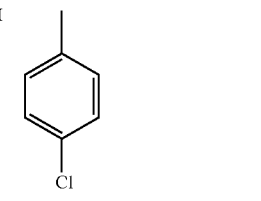 | M.p.: 201–203° C. (decomp.) |
| 4** | H | 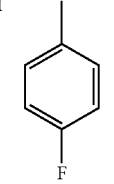 | M.p.: 209–211° C. (decomp.) |
| 5** | H | 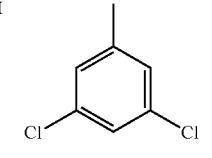 | M.p.: 232–235° C. (decomp.) |
| 6** | H | 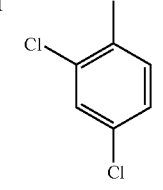 | M.p.: >250° C. |
| 7** | H | 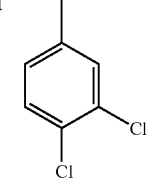 | M.p.: 178–183° C. (decomp.) |
| 8** | H |  | M.p.: 228–233° C. (decomp.) |

**Dihydrochloride

Examples 9–11

The corresponding starting compounds are treated in a similar manner as in Example 1 to give the compounds as listed in Table 2.

TABLE 2

$R^1 = CH_3O—$
$R^2 = CH_3O—$

| Ex. No. | $R^3$ | Ring A | Physiochemical properties |
|---------|-------|--------|---------------------------|
| 9** | —CH$_2$CH$_3$ | phenyl | M.p.: 234–239° C. (decomp.) |
| 10** | —CH$_3$ | phenyl | M.p.: 253–258° C. (decomp.) |
| 11** | ~~~OH | phenyl | M.p.: 242–246° C. (decomp.) |

**Dihydrochloride

Example 12

8,9-Dimethoxy-6-phenyl-1,3,4,6,11,11a-hexahydro-2H-pyrazino[1,2-b]isoquinoline (the compound obtained in Example 1-(6)) (3.2 g) is dissolved in methylene chloride (20 ml), and thereto are added chloromethyl methylsulfide (8.4 ml), triethylamine (3.5 ml) and 4-(dimethylamino) pyridine (61 mg), and the mixture is stirred at room temperature overnight. The reaction solution is washed with a saturated aqueous sodium hydrogen carbonate solution, dried over magnesium sulfate, and concentrated under reduced pressure. The resulting residue is purified by column chromatography on silica gel (eluent; chloroform:ethyl acetate=9:1). The resulting precipitates (115 mg) are dissolved in chloroform, and thereto is added a 4M hydrochloric acid in ethyl acetate, and the solvent is removed by evaporation under reduced pressure. The residue is recrystallized from ethanol to give 8,9-dimethoxy-2-(methylthiomethyl)-6-phenyl-1,3,4,6,11,11a-hexahydro-2H-pyrazino[1,2-b]isoquinoline dihydrochloride (60 mg).

M.p.: 217–220° C. (decomp.)

MS (m/z): 384 (M$^+$)

Example 13

(1) 8,9-Dimethoxy-6-phenyl-1,3,4,6,11,11a-hexahydro-2H-pyrazino[1,2-b]isoquinoline (the compound obtained in Example 1-(6)) (1.6 g) is dissolved in N,N-dimethylformamide (10 ml), and thereto are added potassium carbonate (0.8 g) and methyl bromoacetate (0.5 ml), and the mixture is stirred at room temperature overnight. The reaction solution is diluted with chloroform, washed with a saturated aqueous sodium hydrogen carbonate solution, dried over magnesium sulfate, and concentrated under reduced pressure. The resulting residue is purified by column chromatography on silica gel (eluent; chloroform:ethyl acetate=9:1) to give 8,9-dimethoxy-2-methoxycarbonylmethyl-6-phenyl-1,3,4,6,11,11a-hexahydro-2H-pyrazino[1,2-b]isoquinoline (940 mg).

M.p.: 110–113° C.

MS (m/z): 396 (M$^+$)

(2) The compound obtained in the above (1) (920 mg) is dissolved in tetrahydrofuran (20 ml), and thereto is added a 2M aqueous sodium hydroxide solution (1.3 ml), and the mixture is stirred at room temperature for 3 hours. The mixture is neutralized with a 2M hydrochloric acid, and the solvent is removed by evaporation under reduced pressure. The residue is extracted with chloroform, washed with a saturated brine, dried over magnesium sulfate, and concentrated under reduced pressure. The resulting precipitates (639 mg) are dissolved in chloroform, and thereto is added a 4M hydrochloric acid in ethyl acetate, and the solvent is removed by evaporation under reduced pressure. The residue is recrystallized from ethanol to give 8,9-dimethoxy-2-carboxymethyl-6-phenyl-1,3,4,6,11,11a-hexahydro-2H-pyrazino[1,2-b]isoquinoline dihydrochloride (550 mg).

M.p.: 214–217° C. (decomp.)

MS (m/z): 382 (M$^+$)

Example 14

8,9-Dimethoxy-6-phenyl-1,3,4,6,11,11a-hexahydro-2H-pyrazino[1,2-b]isoquinoline (the compound obtained in Example 1-(6)) (1.6 g) is dissolved in methylene chloride (10 ml), and thereto are added triethylamine (0.8 ml) and benzoyl chloride (0.6 ml) under ice-cooling, and the mixture is stirred for 30 minutes. The reaction solution is washed with a saturated aqueous sodium hydrogen carbonate solution, dried over magnesium sulfate, and concentrated under reduced pressure. The residue is purified by column chromatography on silica gel (eluent; chloroform:ethyl acetate=9:1). The resulting residue is dissolved in chloroform, and thereto is added a 4M hydrochloric acid in ethyl acetate, and the solvent is removed by evaporation under reduced pressure. The resultant is crystallized from ethyl acetate, and the crystals thus obtained are collected by filtration to give 8,9-dimethoxy-2-benzoyl-6-phenyl-1,3,4,6,11,11a-hexahydro-2H-pyrazino[1,2-b]isoquinoline hydrochloride (656 mg).

M.p.: 229–233° C. (decomp.)

MS (m/z): 428 (M$^+$)

Example 15

The corresponding starting compounds are treated in a similar manner as in Example 14 to give the compounds as listed in Table 3.

TABLE 3

R¹ = CH₃O—
R² = CH₃O—

| Ex. No. | R³ | Ring A | Physiochemical properties |
|---|---|---|---|
| 15* | 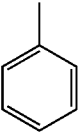 | | M.p.: 187–192° C. (decomp.) |

*Hydrochloride

Example 16

(1) 8,9-Dimethoxy-6-phenyl-1,3,4,6,11,11a-hexahydro-2H-pyrazino[1,2-b]isoquinoline (the compound obtained in Example 1-(6)) (1.6 g) is dissolved in methylene chloride (10 ml), and thereto are added triethylamine (0.8 ml) and benzyloxyacetyl chloride (0.8 ml) under ice-cooling, and the mixture is stirred for 30 minutes. The reaction solution is washed with a saturated aqueous sodium hydrogen carbonate solution, dried over magnesium sulfate, and concentrated under reduced pressure. The resulting residue is purified by column chromatography on silica gel (eluent; chloroform:ethyl acetate=9:1) to give 8,9-dimethoxy-2-benzyloxyacetyl-6-phenyl-1,3,4,6,11,11a-hexahydro-2H-pyrazino[1,2-b]isoquinoline (1.1 g).

M.p.: 100–103° C.

MS (m/z): 472 (M⁺)

(2) To the compound obtained in the above (1) (1.1 g) are added thioanisole (274 µl) and trifluoroacetic acid (20 ml), and the mixture is stirred at room temperature for 2 hours. The reaction solution is concentrated under reduced pressure, and the residue is dissolved in chloroform, washed with a saturated aqueous sodium hydrogen carbonate solution, dried over magnesium sulfate, and concentrated under reduced pressure. The residue is purified by column chromatography on silica gel (eluent; chloroform:acetone=9:1), and the resulting residue (447 mg) is dissolved in chloroform. To the mixture is added a 4M hydrochloric acid in ethyl acetate, and the solvent is evaporated under reduced pressure. The residue is recrystallized from ethanol to give 8,9-dimethoxy-2-hydroxyacetyl-6-phenyl-1,3,4,6,11,11a-hexahydro-2H-pyrazino[1,2-b]isoquinoline hydrochloride (309 mg).

M.p.: 210–214° C. (decomp.)

MS (m/z): 382 (M⁺)

Example 17

(1) 2-[(tert-Butoxy)carbonylamino]acetic acid (1 g) is dissolved in tetrahydrofuran (4 ml), and thereto are added dropwise triethylamine (0.8 ml) and isobutyl chloroformate (0.8 ml) at −20° C., and the mixture is stirred at −10° C. for 5 minutes. To the mixture is added dropwise a suspension of 8,9-dimethoxy-6-phenyl-1,3,4,6,11,11a-hexahydro-2H-pyrazino[1,2-b]isoquinoline (the compound obtained in Example 1-(6)) (1.6 g) in methylene chloride (15 ml), and the mixture is stirred at room temperature overnight. The reaction solution is concentrated under reduced pressure, and extracted with methylene chloride. The extract is washed with a saturated aqueous sodium hydrogen carbonate solution, dried over magnesium sulfate, and concentrated under reduced pressure. The resulting residue is purified by column chromatography on silica gel (eluent; chloroform:ethyl acetate=4:1) to give 8,9-dimethoxy-2-(tert-butoxycarbonyl)aminoacetyl-6-phenyl-1,3,4,6,11,11a-hexahydro-2H-pyrazino[1,2-b]isoquinoline (872 mg).

M.p.: 81–84° C.

MS (m/z): 481 (M⁺)

(2) To the compound obtained in the above (1) (241 mg) is added trifluoroacetic acid (0.5 ml), and the mixture is stirred at room temperature for one hour. To the mixture is added a 4M hydrochloric acid in ethyl acetate, and the reaction solution is concentrated under reduced pressure. To the residue is added toluene, and the mixture is concentrated again under reduced pressure. The resulting residue is recrystallized from a mixed solvent of ethanol and ethyl acetate to give 8,9-dimethoxy-2-aminoacetyl-6-phenyl-1,3,4,6,11,11a-hexahydro-2H-pyrazino[1,2-b]isoquinoline dihydrochloride (190 mg).

M.p.: 228–233° C. (decomp.)

MS (m/z): 381 (M⁺)

Example 18

6,7-Dimethoxy-1-(1-oxypyridin-4-yl)-2,3-bis(acetoxymethyl)naphthalene (2.23 g) is suspended in acetic anhydride (5 ml), and thereto is added 1,3-cyclohexanedione (0.71 g) under ice-cooling. The mixture is stirred at room temperature overnight, and further reacted at 90° C. for 6 hours. The brown reaction solution is cooled to room temperature, and concentrated under reduced pressure. To the residue is added an aqueous sodium hydrogen carbonate solution, and the mixture is extracted with ethyl acetate. The organic layer is washed with brine, dried over magnesium sulfate, and concentrated. The residue is purified by column chromatography on silica gel (eluent; chloroform:acetone=10:1) to give a crude product (1.0 g), which is further purified by Chromatron (solvent; chloroform:acetone=10:1), and crystallized from diethyl ether to give 6,7-dimethoxy-1-[2-(1,3-dioxocyclohexan-2-yl)pyridine-4-yl]-2,3-bis(acetoxymethyl)naphthalene (580 mg).

M.p.: 210–213° C.

Example 19

The compound obtained in Example 18 (440 mg) is suspended in methanol (3 ml), and thereto is added sodium methoxide (28% methanol solution, 0.495 ml) under ice-cooling. The mixture is stirred at room temperature for 30 minutes, during which the mixture is dissolved into a solution but then the crystals precipitate. The reaction solution is cooled with ice, and the pH value thereof is adjusted to pH 4 with a 1M hydrochloric acid. The precipitated crystals are collected by filtration, and washed with water to give 6,7-dimethoxy-1-[2-(1,3-dioxocyclohexan-2-yl)pyridin-4-yl]-2,3-bis(hydroxymethyl)naphthalene (320 mg).

M.p.: >220° C.

EXPERIMENT

Experiment 1

PDE4 Inhibitory Activity (Preparation of Partially Purified PDE4 Specimen)

A homogenate of lung excised from Hartley male guinea pig was centrifuged, and the resulting supernatant was fractionated by anion-exchange chromatography. The fractions satisfying the following conditions 1 to 4 were combined to give a partially purified specimen of phosphodiesterase 4.

Conditions:
(1) having cAMP-selective hydrolyzing activity;
(2) said cAMP hydrolyzing activity being free from the influence of cGMP;
(3) said activity being not inhibited by CI-930 that is a selective PDE3 inhibitor; and
(4) said activity being strongly inhibited by Rolipram that is a selective PDE4 inhibitor.

(Assay for PDE4 Activity)

The assay was carried out in the following manner according to a method of Thompson, et al. (cf. Advances in Cyclic Nucleotide Research, vol. 10, Raven Press, New York, p. 69–92, 1979) with certain modifications. First, partially purified PDE4 specimen (100 μl), which was previously diluted with 50 mM Tris-HCl buffer (pH 8.0) so that about 10% of the total substrate could be hydrolyzed, was put into a glass test tube. To the tube was added a reaction buffer solution (50 mM Tris-HCl, pH 8.0, 12.5 mM $MgCl_2$, 10 mM 2-mercaptoethanol, 200 μl), and thereto was added a solution of a test compound as indicated below in dimethylsulfoxide (100-fold dilution, 5 μl). The tube was pre-incubated at 30° C. for 5 minutes, and thereto was added a 2.5 μM [$^3$H] cAMP (3.7 kBq/200 μl) (200 μl), and the reaction started (the final concentration: 50 mM Tris-HCl, pH 8.0, 5 mM $MgCl_2$, 4 mM 2-mercaptoethanol). After 30-minute-reaction at 30° C., the reaction was quenched by transferring the test tube into a boiling water bath. Ninety seconds later, the test tube was transferred into an ice-water bath to lower the temperature of the reaction solution. After the pre-incubation at 30° C. for 5 minutes, the snake venom (1 mg/ml, 100 μl) was added to the test tube, and the mixture was reacted at 30° C. for 30 minutes. The reaction was quenched by adding methanol (500 μl) thereto, and the reaction solution (1 ml) was charged onto a column of Dowex resin (trade name: Dowex 1×8, manufactured by Sigma, 200 μl). Subsequently, the Dowex resin was washed with methanol (1 ml). The reaction solution passed through the column and the washing of the column were combined, and the radioactivity thereof was measured.

In the blank group, only a buffer was added without the enzyme specimen, and in the control group, the enzyme specimen was added but only dimethylsulfoxide was added instead of a test compound. The inhibitory rate of each test compound as compared with the control group was estimated. The $IC_{50}$ value of each test compound was calculated from the inhibitory rates at 3 or more concentrations using 4-parameter logistic equation according to the regression analysis.

(Test Compounds)
Compound A: 8,9-dimethoxy-6-phenyl-1,3,4,6,11,11a-hexahydro-2H-pyrazino[1,2-b]isoquinoline Compound B: 8,9-dimethoxy-6-phenyl-1,3,4,6,11,11a-hexahydro-2H-pyrazino[1,2-b]isoquinoline dihydrochloride Compound C: (6S,11aS)-8,9-dimethoxy-6-phenyldimethoxy-1,3,4,6,11,11a-hexahydro-2H-pyrazino[1,2-b]isoquinoline dihydrochloride (Results)

The PDE4 inhibitory activity ($IC_{50}$) of each test compound was 0.004 μM.

Experiment 2

Inhibitory Activity Against Antigen-induced Bronchoconstriction (Procedures)

Hartley male guinea pigs (n=2) were passively sensitized with anti-rabbit egg albumin antiserum (0.25 ml/kg body weight, i.v.). On the following day, the guinea pigs were anesthetized with α-chloralose (120 mg/kg, i.v.), and a tracheostomy tube was inserted to the animals. The animals were immobilized with gallamine triethiodide (5 mg/kg, i.v.) under artificial respiration. A test compound (8,9-dimethoxy-6-phenyl-1,3,4,6,11,11a-hexahydro-2H-pyrazino[1,2-b]isoquinoline dihydrochloride) (1 mg/kg) was intravenously administered to the animals 2 minutes prior to the administration of the antigen (egg albumin; 30 μg/kg, i.v.). The influences of the test compound on the trachea (inhibitory activity against bronchoconstriction) was estimated by Konzett-Roessler method (Naunyn-Schmeideberg's Archiv fur Experimentelle Pathologie und Pharmakologie, vol. 195, p. 71, 1940). In the control group, only the antigen was administered to the animals (n=2).

(Results)

The inhibitory activity against bronchoconstriction (i.e., inhibitory rate of bronchoconstriction induced by antigen administration) of the test compound was 84%.

PREPARATIONS

Preparation 1

(1) 2-Amino-3-(3,4-dihydrophenyl)propanoic acid (98.6 g) is dissolved in formic acid (900 ml), and thereto is added acetic anhydride (30.0 ml), and the mixture is stirred at room temperature for 3 hours. The reaction solution is concentrated under reduced pressure, and to the residue is added distilled water, and the mixture is concentrated again under reduced pressure. The residue is dissolved in distilled water (150 ml), and thereto are added a 10M aqueous sodium hydroxide solution (150 ml) and dimethyl sulfate (95 ml). Further, to the mixture are added three portions of dimethyl sulfate (285 ml in total) every 30 minutes, during which a 10M aqueous sodium hydroxide solution (290 ml) is added dropwise, the reaction temperature is kept at below 40° C., and the pH value of the mixture is kept at pH 5 to 9. The mixture is stirred at room temperature overnight, and thereto is added a 10M aqueous sodium hydroxide solution (50 ml), and stirred at room temperature for 30 minutes. The pH value of the mixture is adjusted to pH 2 with sulfuric acid, and thereto is added ethyl acetate. The organic layer is dried over magnesium sulfate, and concentrated under reduced pressure. The residue is suspended in ethanol (1300 ml), and thereto is added dropwise acetyl chloride (280 ml) under ice-cooling. The mixture is stirred at room temperature for 3 days. The solvent is removed by evaporation under reduced pressure, and methylene chloride is added thereto. The organic layer is washed with an aqueous potassium carbonate solution, dried over magnesium sulfate, and concentrated under reduced pressure to give ethyl 2-amino-3-(3,4-dimethoxyphenyl)propionate (111 g) as oil.

MS (m/z): 253 (M$^+$)

(2) The compound obtained in the above (1) (111 g) and triethylamine (73.6 ml) are dissolved in methylene chloride (300 ml), and benzoyl chloride (51.1 ml) is added dropwise thereto under ice-cooling. A saturated aqueous sodium hydrogen carbonate solution is added to the mixture, and the organic layer is washed with a saturated brine, dried over magnesium sulfate, and concentrated under reduced pressure. The precipitated crystals are collected by filtration with diethyl ether to give ethyl 3-(3,4-dimethoxyphenyl)-2-(phenylcarbonylamino)propionate (144 g).

M.p.: 82–83° C.

MS (m/z): 357 (M$^+$)

(3) The compound obtained in the above (2) (71.5 g) is dissolved in phosphorus oxychloride (200 ml), and the mixture is heated under reflux overnight. The phosphorus oxychloride is evaporated under reduced pressure, and the residue is diluted with methylene chloride. The mixture is washed with an aqueous potassium carbonate solution, dried over magnesium sulfate, and concentrated under reduced pressure. The residue is dissolved in ethanol, and conc. hydrochloric acid (20 ml) is added thereto, and the mixture is concentrated under reduced pressure. The residue is dissolved in methanol (200 ml), and thereto is added platinum dioxide (1 g), and the mixture is stirred at room temperature under pressure of hydrogen (3 atms) for 4 hours. The insoluble materials are removed by filtration, and the filtrate is concentrated under reduced pressure. The residue is dissolved in chloroform, washed with a saturated aqueous sodium hydrogen carbonate solution and saturated brine, dried over magnesium sulfate, and concentrated under reduced pressure. The precipitated crystals are collected by filtration to give ethyl 6,7-dimethoxy-1-phenyl-1,2,3,4-tetrahydroisoquinoline-3-carboxylate (54.4 g).

M.p.: 215–217° C. (decomp.)

MS (m/z): 341 (M$^+$)

(4) 2-[(tert-Butoxy)carbonylamino]acetic acid (21.6 g) is dissolved in tetrahydrofuran (75 ml), and thereto are added dropwise triethylamine (18.7 ml) and isobutyl chloroformate (17.4 ml) at −20° C., and the mixture is stirred at −10° C. for 5 minutes. To the mixture is added dropwise a suspension of the compound obtained in the above (3) (38.2 g) in tetrahydrofuran (110 ml), and the mixture is stirred at room temperature overnight. The reaction solution is concentrated under reduced pressure and extracted with chloroform. The extract is washed with a saturated aqueous sodium hydrogen carbonate solution and a saturated brine, dried over magnesium sulfate, and concentrated under reduced pressure. The resultant is crystallized from diethyl ether, and collected by filtration to give ethyl 2-{2-[(tert-butoxy)carbonylamino]acetyl}-6,7-dimethoxy-1-phenyl-1,2,3,4-tetrahydroisoquinoline-3-carboxylate (31.7 g).

M.p.: 166–167° C.

MS (m/z): 498 (M$^+$)

(5) To the compound obtained in the above (4) (31.7 g) is added trifluoroacetic acid (60 ml) under ice-cooling, and the mixture is stirred for one hour. The reaction solution is concentrated under reduced pressure, and the residue is dissolved in chloroform, and neutralized with triethylamine. The mixture is washed with a saturated aqueous sodium hydrogen carbonate solution and a saturated brine, dried over magnesium sulfate, and concentrated under reduced pressure. The residue is dissolved in toluene (350 ml), and the mixture is heated under reflux for 3 hours. The solvent is removed by evaporation under reduced pressure, and the precipitates are collected by filtration with diethyl ether to give 8,9-dimethoxy-6-phenyl-2,3,11,11a-tetrahydro-6H-pyrazino[1,2-b]isoquinoline-1,4-dione (20.6 g).

M.p.: 265–267° C.

MS (m/z): 352 (M$^+$)

(6) Under nitrogen atmosphere, borane-dimethylsulfide complex (22.7 ml) is cooled with ice, and thereto is added dropwise a solution of the compound obtained in the above (5) (20 g) in tetrahydrofuran (500 ml). The mixture is heated under reflux overnight, and thereto is added a 6M hydrochloric acid (50 ml), and the solvent is evaporated under reduced pressure. The residue is diluted with chloroform, washed with an aqueous sodium hydroxide solution, dried over magnesium sulfate, and concentrated under reduced pressure. The resulting residue is purified by column chromatography on silica gel (eluent; chloroform:methanol=9:1). The resulting crystals are dissolved in a mixed solvent of chloroform and methanol, and thereto is added a 4M hydrochloric acid in ethyl acetate, and the solvent is removed by evaporation under reduced pressure. The precipitates are collected by filtration with ethanol to give 8,9-dimethoxy-6-phenyl-1,3,4,6,11,11a-hexahydro-2H-pyrazino[1,2-b]isoquinoline dihydrochloride (7.6 g).

M.p.: 220–224° C. (decomp.)

MS (m/z): 324 (M$^+$)

Preparation 2

Using (2S)-2-Amino-3-(3,4-dihydroxyphenyl)propanoic acid (L-DOPA), the same procedures as Preparation 1 are repeated to give (6S,11aS)-8,9-dimethoxy-6-phenyl-1,3,4,6,11,11a-hexahydro-2H-pyrazino[1,2-b]isoquinoline dihydrochloride.

M.p.: 225–229° C. (decomp.)

MS (m/z): 324 (M$^+$)

INDUSTRIAL APPLICABILITY

The condensed polycyclic compound of the formula [I] or [I-C], or a pharmaceutically acceptable salt thereof of the present invention has an excellent PDE4 inhibitory activity and is useful in prophylaxis or treatment of various PDE4-associated diseases, for example, inflammatory and allergic diseases including asthma, chronic obstructive pulmonary disease (COPD), chronic bronchitis, atopic dermatitis, urticaria, allergic rhinitis, allergic conjunctivitis, vernal conjunctivitis, eosinophilia, psoriasis, rheumatoid arthritis, septic shock, chronic ulcerative colitis, Crohn's disease, reperfusion injury, chronic glomerulonephritis, endotoxic shock, adult respiratory distress syndrome, osteoarthropathy, and the like.

Besides, the compound [I], compound [I-C] or a pharmaceutically acceptable salt thereof, which is an active ingredient of the present invention, has excellent bronchoconstriction inhibitory activity, and is useful as a bronchoconstriction inhibitory agent.

In addition, the compound [I], compound [I-C] or a pharmaceutically acceptable salt thereof is useful as a composition for accelerating bone fracture healing and a composition for treating chondropathia (e.g., osteoarthritis).

What is claimed is:

1. A condensed polycyclic compound of the formula [I]:

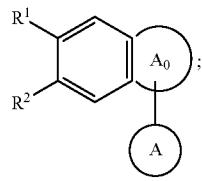

wherein,

R$_1$ and R$_2$ are the same or different and each is a group selected from a hydroxy group or a lower alkoxy group;

ring A$_0$ is a group of the formula:

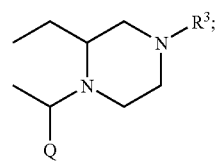

ring A is a substituted or unsubstituted benzene ring or a substituted or unsubstituted 5- to 6-membered monocyclic aromatic heterocyclic ring containing 1 to 3 nitrogen atoms, wherein the substitutents are selected from the group consisting of a lower alkoxy group, a hydroxyl group and a halogen atom;

R$^3$ is:
(1) a hydrogen atom, a group of the formula: —(CH$_2$)$_m$—R$^{31}$ or a group of the formula: —CO—R$^{32}$, when ring A is a substituted benzene ring or a substituted or unsubstituted 5- to 6-membered monocyclic aromatic heterocyclic group containing 1 to 3 nitrogen atoms; or
(2) a group of the formula: —(CH$_2$)$_m$—R$^{31}$ or a group of the formula: —CO—R$^{32}$, when ring A is an unsubstituted benzene ring;

R$^{31}$ is a hydrogen atom, an aryl group, a hydroxy group, an amino group, a carboxyl group, a lower alkoxycarbonyl group or a lower alkylthio group;

R$^{32}$ is an aryl group, a lower alkyl group, a hydroxy-lower alkyl group or an amino-lower alkyl group;

m is an integer of 1 to 6; and

Q is a single bond linked to ring A;

or a pharmaceutically acceptable salt thereof.

2. The compound according to claim 1, wherein R$^1$ and R$^2$ are the same or different and each a lower alkoxy group, ring A is a benzene ring substituted by 1 to 3 groups selected from a lower alkoxy group, a hydroxy group and a halogen atom, and R$^3$ is a hydrogen atom, or a pharmaceutically acceptable salt thereof.

3. The compound according to claim 1, wherein R$^1$ and R$^2$ are each methoxy group, ring A is a benzene ring substituted by 1 to 3 group selected from a isopropyloxy group, a hydroxy group and a halogen atom, and R$^3$ is a hydrogen atom, or a pharmaceutically acceptable salt thereof.

4. 6-[4-(Isopropyloxy)phenyl]-8,9-dimethoxy-1,3,4,6,11,11a-hexahydro-2H-pyrazino[1,2-b]isoquinoline, or a pharmaceutically acceptable salt thereof.

5. 6-(4-Fluorophenyl)-8,9-dimethoxy-1,3,4,6,11,11a-hexahydro-2H-pyrazino[1,2-b]isoquinoline, or a pharmaceutically acceptable salt thereof.

6. A pharmaceutical composition, which comprises as an active ingredient a compound according to any one of claims 1, 2, 3, 4, and 5 or a pharmaceutically acceptable salt thereof and a pharmaceutically acceptable carrier.

7. A pharmaceutically acceptable salt of a pyrazinoisoquinoline compound of the formula [I-C]:

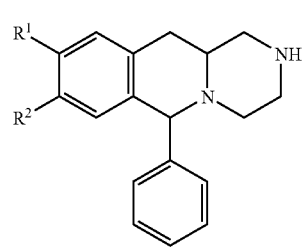

wherein R$^1$ and R$^2$ are the same or different and each is a group selected from a hydroxy group or a lower alkoxy group.

8. A pharmaceutically acceptable salt of 8,9-dimethoxy-6-phenyl-1,3,4,6,11,11a-hexahydro-2H-pyrazino[1,2-b]isoquinoline.

9. 8,9-Dimethoxy-6-phenyl-1,3,4,6,11,11a-hexahydro-2H-pyrazino[1,2-b]isopuinoline dihydrochloride.

* * * * *

UNITED STATES PATENT AND TRADEMARK OFFICE
CERTIFICATE OF CORRECTION

PATENT NO. : 7,153,859 B2  
APPLICATION NO. : 10/486088  
DATED : December 26, 2006  
INVENTOR(S) : Tatsuzo Ukita et al.

Page 1 of 1

It is certified that error appears in the above-identified patent and that said Letters Patent is hereby corrected as shown below:

In claim 9, column 26, lines 46-47, "8,9-Dimethoxy-6-phenyl-1,3,4,6,11,11a-hexahydro-2H-pyrazino[1,2-b]isopuinoline" should read --8,9-Dimethoxy-6-phenyl-1,3,4,6,11,11a-hexahydro-2H-pyrazino[1,2-b]isoquinoline--.

Signed and Sealed this

Twentieth Day of May, 2008

JON W. DUDAS  
*Director of the United States Patent and Trademark Office*